United States Patent [19]
Crovatto

[11] Patent Number: 4,480,996
[45] Date of Patent: Nov. 6, 1984

[54] ENDODONTIC INSTRUMENT FOR DENTAL ROOT CANAL FILLING

[76] Inventor: Richard C. Crovatto, 207 Foxridge Rd., Orange Park, Fla. 32073

[21] Appl. No.: 455,937

[22] Filed: Jan. 4, 1983

[51] Int. Cl.³ .............................................. A61C 3/08
[52] U.S. Cl. ..................................... 433/164; 433/32; 433/81
[58] Field of Search ............................ 433/32, 81, 164

[56] References Cited

U.S. PATENT DOCUMENTS

| | | | |
|---|---|---|---|
| 3,919,775 | 11/1975 | Malmin | 433/32 |
| 4,353,698 | 10/1982 | McSpadden | 433/32 |
| 4,392,827 | 7/1983 | Martin | 433/32 |

*Primary Examiner*—Robert Peshock
*Attorney, Agent, or Firm*—Sixbey, Friedman & Leedom

[57] ABSTRACT

An endodontic instrument for emplacing, heating and condensing a sealing plug in a dental root canal comprises an elongated shank having a heat softenable and deformable root canal sealing plug, desirably formed substantially of gutta percha, detachably affixed to one end of the shank. Elongated retractable conductive means, such as a heat conducting wire, extends longitudinally in the shank and has one end terminating in the plug for detachable affixing the plug to the shank and for causing heating and softening of the plug, the conductive means being slidable in the shank for withdrawing the one end from the plug to enable the shank to be used in condensing the heat softened plug within the dental root canal.

18 Claims, 5 Drawing Figures

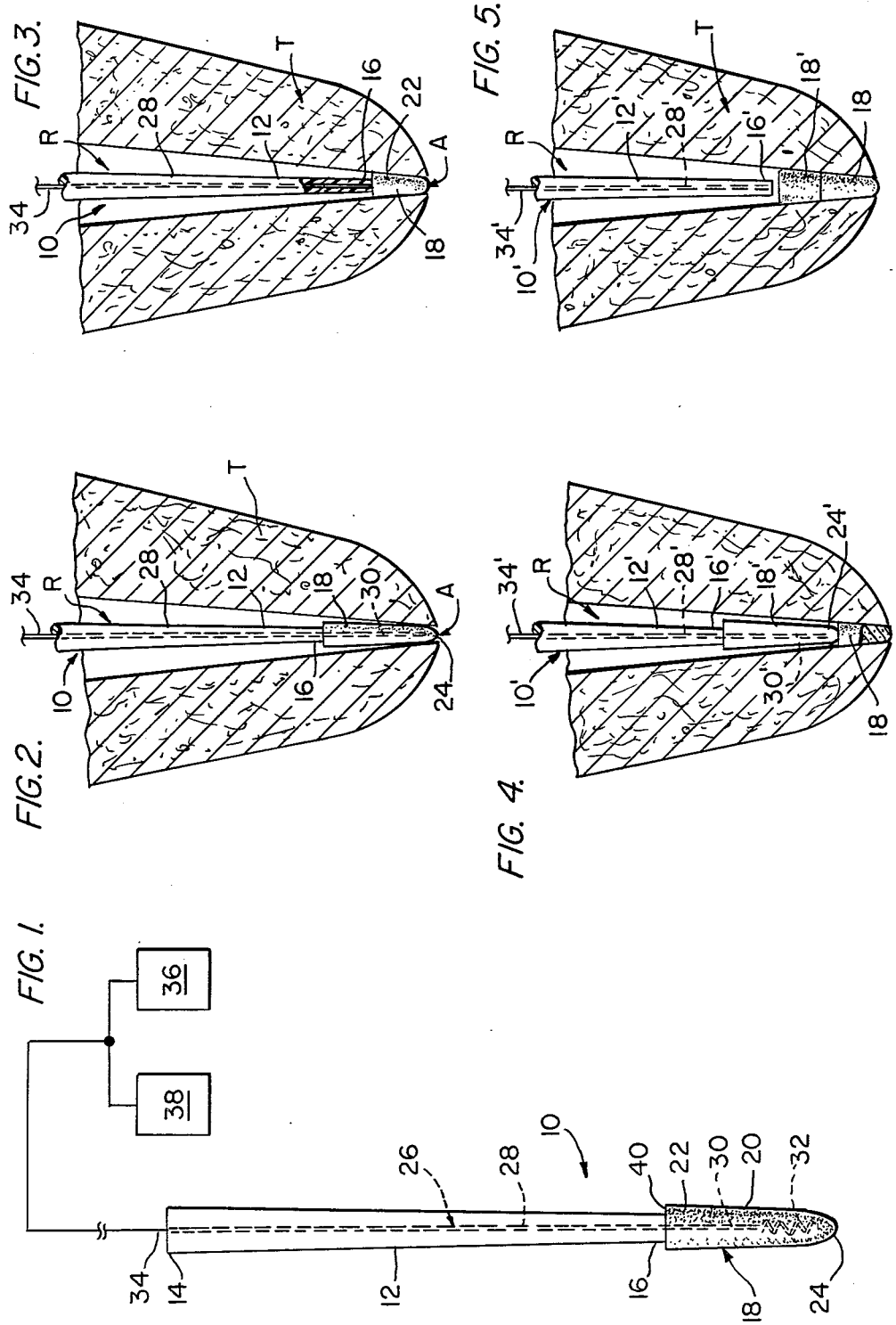

ENDODONTIC INSTRUMENT FOR DENTAL ROOT CANAL FILLING

TECHNICAL FIELD

The present invention relates to endodontics, specifically to root canal therapy and, more particularly, to an instrument for use in simply and efficiently filling a root canal.

BACKGROUND ART

There are two basic stages in the performance of root canal therapy on a tooth. In the first stage the root canal is prepared by conically shaping the walls of the canal using graduated root canal files or reamers. The finished wall has a fairly uniform taper from a largest dimension at the coronal portion of the canal to a narrowest dimension at the apical end thereof. The second stage involves the obliteration of the canal by filling it with cones or plugs formed of a deformable or heat moldable material, most typically gutta percha or some similar thermoplastic material. In one method employed, plugs or cones of gutta percha are placed in the canal and heated to plasticize the gutta percha or heated plugs or cones of gutta percha are placed in the canal. In either case the plasticized gutta percha cones in the canal are condensed with an endodontic plugger to compress and compact the material within the canal to seal the apical end and to fill the void of the root canal. In the well known vertical condensation method a small dimensioned plug or cone is first placed in the canal, plasticized by heat and plunged to the apical end of the canal and compressed with pluggers to fill the apical end. A slightly larger diameter plug or cone is next inserted into the canal above the compressed first cone, plasticized and compressed with the pluggers, and this procedure is continued with progressively larger diameter cones until the canal is filled from the apical end to the desired depth.

Root canal therapy with currently available filling cones and endodontic equipment for plasticizing and compressing the cones involves separate emplacing, heating and condensing steps utilizing multiple endodontic instruments. In particular, the step of and equipment for plasticing the cones is cumbersome and difficult, whether the cones are first heated and then inserted into the canal in their softened condition or first inserted in the canal and then heated by contact with a heated instrument.

It is therefore the purpose of the present invention to overcome these currently encountered practical difficulties and to provide a simple and easy to use instrument for emplacing, heating and condensing heat deformable and moldable plugs or cones in a root canal.

DISCLOSURE OF THE INVENTION

In one aspect of the present invention this is accomplished by providing an endodontic instrument for emplacing, heating and condensing a sealing plug in a dental root canal which comprises an elongated shank having first and second ends, a heat softenable and deformable root canal sealing plug, such as a substantially gutta percha cone, detachably affixed to the first end of the shank and elongated retractable conductive means extending longitudinally in the shank and having one end thereof terminating in the plug for detachably affixing the plug to the shank and for causing heating and softening of the plug, the conductive means being movable in the shank for withdrawing the one end thereof from the plug, whereby the first end of the shank may be used for condensing the heat softened plug within the dental root canal.

In another aspect of the present invention the conductive means is either a heat conducting wire for conducting heat through the shank to the plug or an electrical current conducting wire for conducting electrical current to a heat producing element in the plug.

In a particularly preferred aspect of the invention the plug is generally elongated, the plug and shank are generally circular in cross-section, the plug diameter is smaller at its free end than at the end affixed to the shank and the plug diameter at its affixed end is greater than the shank diameter at its affixed end.

BRIEF DESCRIPTION OF THE DRAWINGS

The invention will be better understood from the following description taken together with the accompanying drawings in which:

FIG. 1 is a vertical sectional view of one form of the endodontic instrument of the present invention.

FIG. 2 is a vertical sectional view of a tooth having a dental root canal showing a first step in filling the dental root canal using the endodontic instrument of the present invention.

FIGS. 3-5 are vertical sectional views of the tooth of FIG. 2 showing subsequent steps in filling the dental root canal using the endodontic instrument of the present invention.

BEST MODE FOR CARRYING OUT THE INVENTION

The present invention provides a simple and efficient method for filling a dental root canal with heat softenable and deformable sealing plugs using a single endodontic instrument for emplacing, heating and condensing the plugs within the root canal. The dental root canal is prepared for filling in the conventional manner, removing debris and shaping the canal using conventional endodontic reamers and files. As is well known in the art the reamers and files are commercially available in a variety of standard sizes having standardized dimensions and specifications. A multiplicity of sealing plugs, preferably conforming in size to the standardized dimensions and specifications of the endodontic files and reamers, are individually and serially emplaced in the root canal, heated to softening and condensed until the canal is vertically filled to the level desired.

In accordance with the present invention the emplacing, heating and condensing of the sealing plugs is advantageously accomplished using the endodontic instrument 10 shown in FIG. 1. Instrument 10 consists of an elongated shank 12 having opposite ends 14,16 and preferably coaxially mounting a root canal sealing plug 18 at one end 16. The body of plug 18 is formed of a heat softenable and deformable material, such as gutta percha or some similar thermoplastic material, and is in the general form of a truncated cone having a generally conically tapering wall 20 extending from end 22, mounted on shank end 16, toward free end 24. In a preferred form of the invention the cross sectional configuration of plug 18 in a plane perpendicular to its longitudinal axis is generally circular, although this need not be the case. In a similar manner the shank 12, preferably made from heat resistant plastic, preferably tapers uniformly from end 14 toward end 16 and desirably has a cross sectional configuration in a plane perpendicular to its longitudinal axis which is generally circular, although this need not be the case, and shank 12 may have any lengthwise or cross sectional configuration which is consistent with its use as an endodontic instrument as hereinafter described. A relatively small diameter conductive means 26 extends longitudinally, preferably centrally, through shank 12 into plug 18, extending entirely or nearly to free end 24 for causing heating of plug 18 to soften the plug. Desirably, conductive means 26 is a small diameter conductive wire 28 extending longitudinally in shank 12 between its ends 14,16 and having one end 30 thereof terminating in plug 18 for detachably affixing plug 18 to shank end 16. In one embodiment of the invention, wire 28 is adapted for conducting heat to plug 18 for heating plug 18 to its softening point (about 140° F. for gutta percha). In another embodiment of the invention, wire 28 is adapted for conducting electric current to a heat producing element in plug 18, such as small diameter resistive element 32, shown in phantom in FIG. 1, which is retractable from plug 18 with wire 28. In still other embodiments of the invention conductive means 26 may be any means for conducting heat or energy to plug 18 to cause the heating thereof, for example an optical fiber conducting laser energy to plug 18. Conductive means 26 is retractable from plug 18 after plug 18 has been heated to its softening temperature. To facilitate withdrawal of end 30 of conductive means 26 from softened plug 18, it is convenient, for example, for the other end 34 of wire 28 to project from shank 12 whereby it may be grasped by retracting means 36 for sliding wire 28 through shank 12 until end 30 is withdrawn from plug 18. The retracting means 36 may be manually operated forceps held by the dentist or an instrument specially designed for retracting wire 28 using remotely operated means, such as lever means or the like. Thermal energy, electrical power or other energy forms conductive via conductive means 26 for causing heat softening of plug 18 is readily furnished to wire 28 via its end 34 by thermal energy or power source 38.

INDUSTRIAL APPLICABILITY

The endodontic instrument 10 is broadly applicable in root canal filling procedures as can be seen most clearly from FIGS. 2-5 which illustrate, in generally vertical section, a portion of a typical tooth T having a root canal R therein which is formed in a generally conical shape by the use of graduated endodontic reamers and files to have a generally uniform taper toward its apical end A. The root canal R is generally packed in the manner hereindescribed, with a series of 3-5 mm long gutta percha cones conforming in diameter to the specifications used in the manufacture of the endodontic files and reamers and, at the option of the dentist, with some cement. As can be seen in FIG. 1, the first gutta percha cone is placed within root canal R by inserting therein shank 12 having gutta percha cone 18 affixed to the end thereof by small diameter wire 28 which is embedded longitudinally within shank 12 and has an end 30 extending into plug 18. In addition to affixing plug 18 to shank 12 and conducting heat through shank 12 to soften plug 18, wire 28 confers a desired rigidity on plug 18 to allow it to follow narrow, curved and tortuous contours of a root canal without interfering with the necessary flexibility of the plug. Free end 24 of plug 18 is placed at the apical end A of canal R with shank 12 also extending into canal R. It is, therefore, important that the dimensions of shank 12 allow it to be readily insertable within the root canal and, for this purpose, it is desirable that shank 12 substantially conforms in shape and taper to the endodontic files and reamers used to shape the canal. Controlled heat is applied to gutta percha plug 18 from thermal energy source 38 via end 34 of wire 28, causing the gutta percha to soften within the root canal cavity. With the gutta percha softened, wire end 30 is withdrawn from plug 18 by a retracting force applied to wire end 34 by retracting means 36, causing wire 28 to slide longitudinally in shank 12 until wire end 30 no longer projects through end 16 of shank 12. Without wire 28 affixing plug 18 to shank 12, the shank is readily freed from the plug within the root canal to allow shank 12 to function as a plugger. To facilitate the separation of shank 12 and plug 18 it may be desirable, although not necessary, to coat at least the end 16 of shank 12 with a non-sticking substance, such as Teflon.

FIG. 3 illustrates a plug 18 condensed by end 16 of shank 12 into the apical end A of root canal R to sealingly pack the apical end of the canal with the softened gutta percha until it conforms to the contours of the canal wall. Wire 28 is fully withdrawn into the end 16 of shank 12 prior to condensation to prevent voids in the gutta percha after condensation and in order that it does not interfere with the condensation of the gutta percha. In order to effectively act as an endodontic plugger, shank 12 must be sufficiently rigid that a condensing force can be applied thereto and, through it, to the softened gutta percha. At the same time, the shank must have some flexibility so that it can negotiate curved canals and, as already indicated, be so dimensioned that it is readily insertable within root canal R. In addition, it is desirable that shank end 16 have a smaller maximum cross sectional dimension than the maximum cross sectional dimension of the plug it inserts into the root canal in order to assure that the shank end 16 can effectively condense any plug 18 it may insert without interference from the root canal walls. In the embodiment illustrated, wherein plug 18 and shank 12 are both generally circular in cross section, the diameter of shank end 16 is desirably smaller than the diameter of adjacent plug end 22, defining a circumferential shoulder 40 at the shank end-plug end intersection. After shank 12 has been used to condense the plug 18 which it has inserted it is withdrawn from canal R and discarded. Another instrument 10', having a larger dimensioned plug 18' and shank 12' is next inserted within root canal R until plug end 24' is adjacent the condensed plug 18 from the previous insertion, as shown in FIG. 4. Again, controlled heat is applied by thermal energy means 38 via end 34' of embedded wire 28' to soften gutta percha plug 18' until it is sufficiently softened that retracting means 36 is able to withdraw wire end 30' from plug 18' into shank 12' and end 16' of shank 12' is separable from plug 18'. Shank 12' is then used as a plunger or plugger to condense softened plug 18' on top of plug 18 to conform plug 18' to the contours of the root canal wall, as is shown in FIG. 5. Shank 12' is then withdrawn and discarded. This vertical condensation procedure is continued with multiple instruments 10 serially inserting multiple gutta percha plugs 18 until the root canal R is vertically filled to any desired level of the canal and to allow a post to be constructed therein.

I claim:

1. An endodontic instrument for emplacing, heating and condensing a sealing plug in a dental root canal comprising:
    an elongated shank having first and second ends said first end of said shank being dimensioned to be insertable within the dental root canal and adapted for having a heat softenable and deformable root canal sealing plug detachably affixed thereto;
    elongated retractable conductive means extending longitudinally in said shank, said conductive means being movable in said shank for causing one end thereof to project through said first end, said projecting end adapted for insertion into said plug in direct contact therewith for detachably affixing said plug to said shank and for causing heating of said plug to soften said plug, said conductive means being movable in said shank for withdrawing said one end thereof from said plug and into said shank for releasing said plug from said shank and providing a free end of said shank for condensing said heat softened plug within the dental root canal.

2. An instrument as claimed in claim 1, wherein said conductive means is a heat conducting wire for conducting heat to said plug.

3. An instrument as claimed in claim 2, wherein the other end of said wire is adapted for thermal communication with a source of thermal energy.

4. An instrument as claimed in claim 3, wherein the other end of said wire extends from said second end of said shank.

5. An instrument as claimed in claim 1, including a heat producing element in said plug and wherein said conductive means is an electrical current conducting wire for conducting electrical current to said heat producing element.

6. An instrument as claimed in claims 1, 2, 3 4 or 5, wherein said shank tapers substantially uniformly along its length between a minimum cross-sectional area at said first end and a maximum cross-sectional area at said second end.

7. An instrument as claimed in claims 1, 2, 3, 4 or 5, wherein the maximum cross-sectional dimensions of said first end of said shank is smaller than the maximum cross-sectional dimension of said plug.

8. An instrument as claimed in claim 6 wherein the maximum cross-sectional dimension of said first end of said shank is smaller than the maximum cross-sectional dimension of said plug.

9. An instrument as claimed in claim 8, wherein said plug is generally elongated having one free end and the other end affixed to said shank, said plug tapering substantially uniformly along its length between a minimum cross-sectional area at said free end and a maximum cross-sectional area at its other end.

10. An instrument as claimed in claim 9, wherein said plug is generally circular in cross-section and the diameter of said plug at its free end is smaller than the diameter of said plug at its other end.

11. An instrument as claimed in claim 10, wherein said shank is generally circular in cross section and the diameter of said shank at its first end is smaller than the diameter of said plug at its other end.

12. An instrument as claimed in claims 1, 2, 3, 4 or 5, wherein said plug and said shank are substantially coaxial.

13. An instrument as claimed in claim 7, wherein said plug and said shank are substantially coaxial.

14. An instrument as claimed in claim 11, wherein said plug and said shank are substantially coaxial.

15. An instrument as claimed in claims 1, 2, 3, 4 or 5, wherein said plug is substantially gutta percha.

16. An instrument as claimed in claim 7, wherein said plug is substantially gutta percha.

17. An instrument as claimed in claim 11, wherein said plug is substantially gutta percha.

18. An instrument as claimed in claim 13, wherein said plug is substantially gutta percha.

* * * * *